United States Patent [19]

Wilson et al.

[11] Patent Number: 5,041,384

[45] Date of Patent: Aug. 20, 1991

[54] PICHIA GUILLIERMONDII (ANAMORPH CANDIDA GUILLIERMONDII) USEFUL FOR THE BIOLOGICAL CONTROL OF POSTHARVEST ROTS IN FRUITS

[75] Inventors: Charles L. Wilson, Frederick, Md.; Edo Chalutz, Rishonle 'Zion, Italy

[73] Assignees: The United States of Americas as represented by the Secretary of the Agriculture, Washington, D.C.; The State of Israel, ARO/PERI, Israel, Israel

[21] Appl. No.: 530,381

[22] Filed: May 30, 1990

Related U.S. Application Data

[63] Continuation-in-part of Ser. No. 387,669, Jul. 31, 1989, abandoned, which is a continuation-in-part of Ser. No. 177,236, Apr. 4, 1988, abandoned.

[51] Int. Cl.$^5$ ............................ C12R 1/84; C12N 1/16
[52] U.S. Cl. ..................................... 435/255; 434/938; 424/93
[58] Field of Search ....................... 435/921, 938, 255; 424/93

[56] References Cited

U.S. PATENT DOCUMENTS

| | | | |
|---|---|---|---|
| 3,738,488 | 6/1973 | Hondermark | 435/261 |
| 3,764,676 | 10/1973 | Kerst et al. | 514/112 |
| 3,917,476 | 11/1975 | Kerst et al. | 71/67 |
| 4,764,371 | 8/1988 | Pusey et al. | 424/93 |
| 4,950,472 | 8/1990 | Janisiewicz | 424/93 |
| 4,975,277 | 12/1990 | Janisiewicz | 424/93 |

*Primary Examiner*—Herbert J. Lilling
*Attorney, Agent, or Firm*—David R. Sadowski; M. Howard Silverstein

[57] ABSTRACT

The present invention is drawn to processes for biologically controlling postharvest disease in fruit using isolates of *Pichia guilliermondii* having the identifying characteristics of NRRL Y-18313, NRRL Y-18314, and NRRL Y-18654. The organisms were isolated from the surface of citrus fruits and are useful to control a variety of fruit-rot pathogens in a variety of fruits. Also disclosed is a biologically pure culture of at least one isolate of *Pichia guilliermondii* having the identifying characteristics of an isolate selected from the group consisting of NRRL Y-18313, NRRL Y-18314, and NRRL Y-18654.

4 Claims, 2 Drawing Sheets

Values followed by different letters are significantly different at a level of 1% according to Duncan's Multiple Range Test.

PICHIA GULLIERMONDII (ANAMORPH CANDIDA GUILLIERMONDII) USEFUL FOR THE BIOLOGICAL CONTROL OF POSTHARVEST ROTS IN FRUITS

CROSS-REFERENCE TO RELATED APPLICATIONS

This application is a continuation-in-part of Ser. No. 07/387,669 filed July 31, 1989 which is a continuation-in-part of Ser. No. 07/177,236 filed Apr. 1, 1988, both now abandoned.

OTHER RELATED APPLICATIONS

The present application is a continuation-in-part of application Ser. No. 07/177,236 filed Apr. 4, 1988 entitled "Biological Control of Postharvest Rots in Fruits Using *Debaryomyces hansenii*" by Charles Wilson and Edo Chalutz. This application also relates to the subject matter of applications: Ser. No. 07/387,669 filed July 31, 1989 entitled "Inhibiting Plant Pathogens with Nonantibiotic Antagonistic Microorganism(s)" by Charles Wilson and Edo Cahlutz which is a continuation-in-part of the aforementioned application Ser. Nos. 07/177,236; and 07/395,681 filed Aug. 18, 1989 entitled "Inhibiting Plant Pathogens with an Antagonistic Microorganism(s)" by Randy McLaughlin, Charles Wilson and Edo Chalutz, which is a continuation-in-part of the aforementioned applications Ser. Nos. 07/387,669 and 07/177,236.

BACKGROUND OF THE INVENTION

1. Field of the Invention

The present invention relates to the biological control o postharvest diseases in fruit. More particularly, this invention relates to a method for biologically controlling postharvest rots on fruits using strains of *Pichia guilliermondii* (anamorph *Candida guilliermondii*).

2. Description of Prior Art

Postharvest diseases of fruit cause 15 to 25% losses yearly in the fruit industry worldwide. Fungicides, the major weapon in combatting these diseases, are often ineffective and pose hazards to humans and the environment. Therefore, a critical need exists for new methods to control postharvest diseases.

Recently, it has been shown that the postharvest treatment of fruit with antagonistic microorganisms is an effective approach to the control of postharvest rots. Remarkable success was shown in the control of brown rot in peaches caused by *Monilinia fructicola* (Wint.) Honey with *Bacillus subtilis*. Pusey et al. [Plant Dis. 86:753-756 (1986)]. De Matos was able to reduce mold incidence from 35% to 8% when a species of Trichoderma was inoculated with *Penicillium digitatum* into lemon peel. De Matos, Ph.D. Dissertation, University of California, Riverdale, (1983). Singh and Deverall demonstrated biocontrol with bacterial antagonists to the citrus pathogens *Alternaria citri* Pierce, *Geotrichum candidum* link. ex Pers., and *P. digitatum*. Singh et al. [Trans. Br. Mycol. Soc. 83:487-490 (1983)]. Dipping wounded citrus fruit in suspensions of bacterial cells, particularly a strain of *Bacillus subtilis* (Ehrenber) Cohn, delayed decay by the three rot pathogens.

SUMMARY OF THE INVENTION

We have discovered new strains of *Pichia ouilliermondii* (anamorph *Candida guilliermondii*) which are highly effective in controlling a variety of fruit-rot pathogens which affect several species of fruit. Three isolates of the new strains have been deposited with the culture collection at The Northern Regional Research Center, U.S. Department of Agriculture, Peoria, Illinois 61604, under the acquisition numbers NRRL Y-18313, and NRRL Y-18314, and NRRL Y-18654. NRRL Y-18313 and NRRL Y-18314 were both deposited on Feb. 16, 1988 and NRRL Y-18654 was deposited on May 16, 1990. These isolates have been identified as *Pichia guilliermondii* (anamorph *Candida guilliermondii*). The deposited materials have been accepted for deposit under the *Budapest Treaty* on the International Recognition of the Deposit of Microorganisms for the purposes of patent procedures. Further, (1) said depositary affords permanence of the deposits and ready accessibility thereto by the public if a patent is granted, (2) the materials have been deposited under conditions that assure that access to the materials will be available during the pendency of the patent application to one determined by the Commissioner of Patents and Trademarks to be entitled thereto under 37 CFR 1.14 and 35 USC 122. All restrictions on the availability of progenies of the strain to the public will be irrevocably removed upon the granting of the patent.

Accordingly, it is an object of the present invention to provide a novel biological control agent which is safe and highly effective to control a variety of postharvest diseases in a variety of fruits.

It is also an object of the invention to provide a method of biologically controlling postharvest diseases in fruits which eliminates the use of fungicidal treatments.

In accordance with our invention, fruits are subjected to an aqueous suspension comprised of at least one isolate of *Pichia guilliermondii* having the identifying characteristics of an isolate selected from the group consisting of NRRL Y-18313, NRRL Y-183144, and NRRL Y-18654. In effect, the organisms multiply and occupy the surfaces of wounded fruit, thereby preventing infection by fruit-rot pathogens.

DESCRIPTION OF THE PREFERRED EMBODIMENTS

Figure 1:
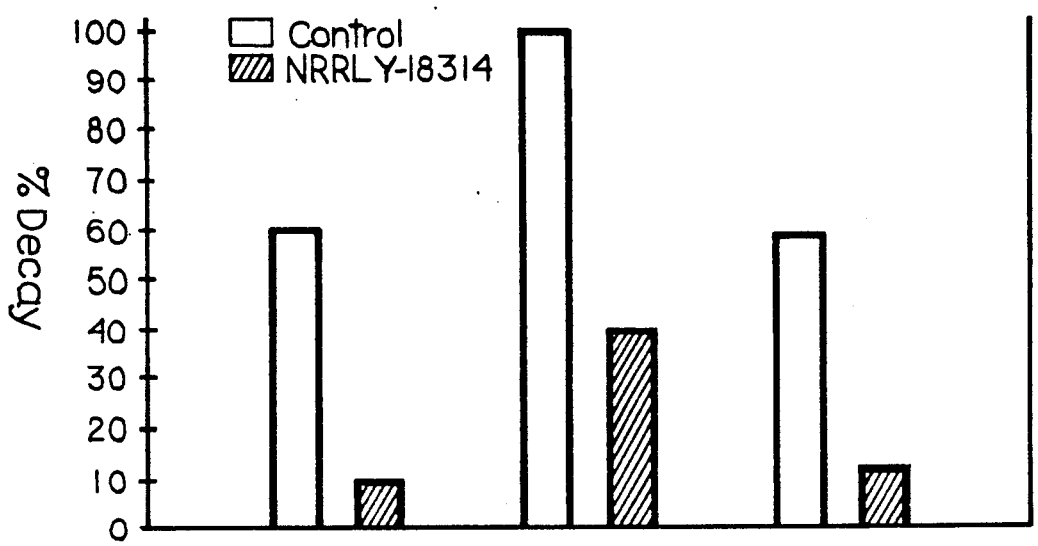
FIG. 1 is a bar graph of percent decay of three lots of grapes treated with NRRL Y-18314 and grapes in a control group, showing inhibition of Rhizopus rot.

Isolates NRRL Y-18313 and NRRL Y-18314 were obtained from the surface of citrus fruits by repeatedly washing the fruit with water. Isolate NRRL Y-18654 was obtained from the surface of a lemon by repeated washings. The organisms are thereafter plated and grown on any nutritionally rich medium sufficient to support growth of microorganisms. Preferably, the medium is either yeast dextrose agar (NYDA) or yeast-malt extract agar (YM).

Isolates NRRL Y-18313 AND NRRL Y-18314 have the following identifying characteristics: Colonies are cream white, slightly raised, shiny, round and smooth. No pseudohyphae were observed.

No ascospores were produced after one week on Corn Meal agar, V-8 Juice agar, YM or acetate. On solid YM, cells are unicellular in liquid culture after one day. Small globose cells are observed mainly in chains or clusters, many with one bud. Isolate NRRL Y-18654 colonies are cream white, slightly raised, shiny, round with smooth edges.

Biochemical and physiological tests of the isolates were as follows:

| | NRRL Y-18314 | NRRL Y-18313 | NRRL Y-18654 |
|---|---|---|---|
| Carbon Assimilation: | | | |
| Glucose | + | + | + |
| Galactose | + | + | + |
| L-sorbose | + | + | + |
| Maltose | + | + | + |
| Sucrose | + | + | + |
| Cellobiose | + | + | + |
| Trehalose | + | + | + |
| Lactose | − | − | − |
| Melibiose | + | − | + |
| Raffinose | + | + | + |
| Melezitose | + | + | + |
| Inulin | + | + | + |
| Soluble Starch | w | w | + |
| D-xylose | + | + | + |
| L-arabinose | + | + | + |
| D-arabinose | + | + | + |
| D-ribose | + | + | + |
| L-rhamnose | + | w | + |
| D-gluco-samine | + | w | + |
| Ethanol | w | w | + |
| Erythritol | w | − | − |
| Glycerol | + | + | + |
| Adonitol (Ribitol) | + | + | + |
| Dulcitol (Galactitol) | + | + | + |
| D-mannitol | + | + | + |
| D-sorbitol (glucitol) | + | + | + |
| a-methly-D-glucoside | + | + | + |
| Salicin | + | + | + |
| Inositol | − | − | − |
| Lactic acid | w | + | − |
| Citric acid | + | + | + |
| Succinic acid | + | + | + |
| Nitrogen assimilation: | | | |
| NH$_4$NO$_3$ | + | + | + |
| KNO$_3$ | + | + | +(weak) |
| NO$_2$ | w | w | − |
| Ethylamine | + | + | + |
| Fermentation: | | | |
| Glucose | + | + | + |
| Galactose | w | + | − |
| Maltose | − | − | − |
| Sucrose | + | + | + |
| Lactose | − | − | − |
| Raffinose | − | − | +/− |
| Melibiose | − | − | − |
| Inulin | w | − | − |
| Cellobiose | − | − | − |
| Melezitose | − | − | − |
| Starch | − | − | − |
| Trehalose | − | − | − | w = weak

Growth of the organisms is effected under aerobic conditions at any temperature satisfactory for growth of the organisms; i.e. from about 10° C. to about 30° C. The preferred temperature range is about 20° C. to 25° C. The pH of the nutrient medium is about neutral; i.e. 6.7 to 7.2. The incubation time is that time necessary for the organisms to reach a stationary phase of growth. Incubation time is preferably from about 40 to 60 hours for NRRL Y-18314 and NRRL Y-18313. Incubation time is preferably from about 24 to 48 hours for NRRL Y-18654.

Isolates NRRL Y-18313, NRRL Y-18314, and NRRL Y-18654 may be grown in any conventional shake flask for small fermentation runs. For large scale operations, it is convenient to carry out the culture in a fermentation tank, while applying agitation and aeration to the inoculated liquid medium. Following incubation, the organisms are harvested by conventional sedimentary methodology; i.e. centrifugation or filtering. Cultures are stored on silica gel and frozen until use.

Isolates NRRL Y-18313, NRRL Y-18314, and NRRL Y-18654 are useful to control a variety of fruit-rot pathogens which cause postharvest diseases in fruits. Exemplary species of fruit-rot pathogens include, but are not limited to, *Penicillium italicum* Wehmer, *Penicillium digitatum*, *Botyrtis cinerea*, *Rhizopus stolonifer*, *Geotrichum candidum*, *Penicillium expansum*, and *Alternaria alternata*.

The organisms of the invention are useful to control postharvest diseases in a variety of fruit including, but not limifed to, all cultivars of citrus fruits, grapes, apples, pears, tomatoes, persimmons and the like. Suitable citrus fruits include, but are not limited to, grapefruits, oranges, lemons and the like.

The organisms of the invention are preferably applied to the fruits in suspension with water. When grown in a liquid medium, the organisms may be applied in suspension with the liquid medium. Suspensions of the organisms of the invention may also include conventional additives such as: surfactants and wetting agents to enhance the effectiveness of the organisms. As an integrated approach, the organisms of the present invention may be used with a very low concentration of a fungicide.

Concentrations of suspensions useful in the invention are any concentrations which inhibits the development of the targeted fruit-rot pathogen when applied to the fruit. As will be obvious to one skilled in the art, effective concentrations may vary depending upon such factors as: (1) the type of fruit; (2) the ripeness of the fruit; (3) the concentration of pathogens affecting the fruit; (4) the type of wound on the fruit; (5) temperature and humidity; and (6) the age of the fruit-rot pathogen. Exemplary concentrations range from about $1 \times 10^4$ to $1 \times 10^9$ CFU/ml, most preferably, from about $1 \times 10^7$ to $1 \times 10^9$ CFU/ml. For purposes of the invention, the abbreviation "CFU" is used herein to designate "colony forming units."

The organisms of the invention may be applied to fruits using conventional methods such as dipping, spraying or brushing. In addition, the organisms of the invention may be incorporated into waxes, wraps or other protective coatings used in processing the fruits.

The fruits may be treated anytime before or after harvest. Typically, the preferred time of treatment is after harvest and prior to storage or shipment. In the case of some grapes, the preferred time of treatment is before harvest.

It is within the scope of the invention to treat the fruits with isolates NRRL Y-18313, NRRL Y-18314, or NRRL Y-18654 alone, or in combination (i.e. at least one isolate of *Pichia guilliermondii* having the identifying characteristics of an isolate selected from the group consisting of NRRL Y-18313, NRRL Y-18314, and NRRL Y-18654 e.g. including a mixture of two or more such isolates). The organisms may also be used in combination with other control agents useful to inhibit the development of fruit-rot pathogens on fruits. When used, these agents should be used in an amount, as readily determined by one skilled in the art, which will not interfere with the effectiveness of the organisms of the invention.

The following examples are intended to further illustrate the invention and not to limit the scope of the invention as defined by the claims.

EXAMPLE I

The effectiveness of Pichia quilliermondii NRRL Y-18314 was evaluated using the following seven citrus cultivars: grapefruit (*Citrus paradisi* Macf. cv 'Marsh Seedless'); 'Shamouti' and 'Valencia' orange (*C. sinensis* Osbeck); lemon (*C. lemon* L. Burm 'Eureka'); Temple orange (Tanger hybrid, *C. reticulata* ' X *C. sinensis*); Kumquat (*Fortunella margarita*); and pummelos, (*C. grandis*). Fruit rot pathogens tested included *Penicillium digitatum*, *Penicillium italicum* and *Geotrichum candidum* Link. ex Pers., fungi responsible for the postharvest diseases green-mold, blue-mold and sour-rot, respectively.

A biologically pure culture of isolate NRRL Y-18314 was obtained using the following procedures: The surface of lemons was washed by placing the fruit in a 600 ml beaker containing 200 milliliters (ml) of sterile water. The beakers containing the fruit were placed on a rotary shaker at 100 rpm for 10 minutes. One tenth ml of the wash water was then spread on a NYDA plate and allowed to incubate for 24 hours before colonies were selected. The same fruit received three separate washings and the same procedures were followed. Appearing colonies were isolated and purified using standard purification techniques. All cultures were stored on silica gel in a freezer until use. NRRL Y-18313 and NRRL Y-18654 may be obtained using similar procedures.

Isolate NRRL Y-18314 was grown in flasks containing nutrient yeast dextrose broth (NYDB) on a reciprocal shaker at 30° C. for 48 hours. The culture was centrifuged at 7000 rpm for 10 minutes and the resulting pellet was suspended in water at various concentrations. Concentrations of the aqueous suspensions were adjusted on a spectrophotometer.

Freshly harvested fruit was wiped with 95% ethanol and placed on moist paper in 50×100×15 cm plastic trays, 24 fruits per tray. Two to four conical wounds, 3mm deep, were cut in the fruit peel. The wounds were brushed with an aqueous suspension of NRRL Y-18314. Concentrations of the aqueous suspensions ranged from $1 \times 10^5$ to $1 \times 10^{10}$ CFU/ml. One to two hours later, 20 microliters of an aqueous spore suspension of the targeted pathogen, $1 \times 10^4$ spores/ml, were pipetted into the wounds. Control fruits were inoculated with aqueous spore suspensions of the targeted pathogen only. Following incubation, the trays were covered with high density polyethylene sleeves and kept at room temperature for several days.

The number of inoculated sites on which decay developed was determined daily. Each treatment in each experiment consisted of at least 3 replicates of 6 fruits, 24 to 75 inoculation sites per treatment. Each experiment was repeated at least twice.

The results are given in Tables I, II, and III:

TABLE I

Relative effectiveness of *Pichia guilliermondii* NRRL Y-18314 in inhibiting *Penicillium digitatum* decay of different citrus cultivars.

| Citrus cultivar | Antagonist | Incubation time (days) | | | |
|---|---|---|---|---|---|
| | | 4 | 5 | 6 | 7 |
| | | Percent Infection[a] | | | |
| Grapefruit | NRRL Y-18314 | 0 | 2 | 6 | 11 |
| (72) | Control | 90 | 97 | 100 | 100 |
| Orange, "Shamouti" | NRRL Y-18314 | 0 | 3 | 10 | 17 |
| (42) | Control | 93 | 100 | 100 | 100 |
| Orange, "Valencia" | NRRL Y-18314 | 2 | 4 | 8 | 17 |
| (42) | Control | 90 | 94 | 97 | 100 |
| Lemon | NRRL Y-18314 | 0 | 2 | 10 | 15 |
| (42) | Control | 98 | 100 | 100 | 100 |
| Temple | NRRL Y-18314 | 2 | 4 | 10 | 14 |
| (48) | Control | 95 | 96 | 99 | 100 |
| Pummelo | NRRL Y-18314 | 0 | 0 | 2 | 2 |
| (24) | Control | 83 | 90 | 92 | 96 |
| Kumquat[b] | NRRL Y-18314 | 4 | 8 | 12 | — |
| (150) | Control | 19 | 23 | 37 | — |

[a]Number of inoculation sites per treatment is indicated in parentheses under the cultivar's name.
[b]Whole fruits were used without artificial inoculation. The fruit was dipped momentarily in a 48 hr-old liquid culture of the NRRL Y-18314. NYDB was used as control.

TABLE II

Inhibition of *Penicillium italicum* decay of grapefruit and orange by *Pichia guillermondii*, NRRL Y-18314

| Citrus cultivar | Antagonist | Incubation time (days) | | | |
|---|---|---|---|---|---|
| | | 3 | 4 | 5 | 6 |
| | | Percent Infection[a] | | | |
| Grapefruit | NRRL Y-18314 | 3 | 3 | 4 | 6 |
| (72) | Control | 97 | 100 | 100 | 100 |
| Orange "Valencia" | NRRL Y-18314 | 3 | 8 | 10 | 19 |
| (72) | Control | 84 | 95 | 97 | 100 |
| Orange "Shamouti" | NRRL Y-18314 | 3 | 6 | 8 | 15 |
| (72) | Control | 90 | 95 | 100 | 100 |

[a]Number of inoculation sites per treatment is indicated in parentheses under the cultivar's name.

TABLE III

Inhibition of *Geotrichum candidum* decay of grapefruit and lemon by *Pichia quillermondii*, NRRL Y-18314

| Citrus cultivar | Antagonist | Incubation time (days) | | | |
|---|---|---|---|---|---|
| | | 3 | 4 | 5 | 6 |
| | | Percent infection[a] | | | |
| Grapefruit | NRRL Y-18314 | 3 | 3 | 8 | 9 |
| (72) | Control | 30 | 56 | 78 | 86 |
| Lemon | NRRL Y-18314 | 12 | 17 | 18 | 18 |
| (30) | Control | 75 | 77 | 77 | 77 |

[a]Number of inoculation sites per treatment is indicated in parentheses under the cultivar's name.

As shown in Table I, isolate NRRL Y-18314, was highly effective in inhibiting *Penicillium digitatum* decay on citrus fruit in all cultivars tested. The effectiveness of NRRL Y-18314 varied depending upon the sensitivity of the cultivar to the decay. When compared to its effectiveness on grapefruit, isolate NRRL Y-18314 was more effective on pummelo fruit but less effective on temple, lemon, orange, or kumquat fruits.

Table II shows that isolate NRRL Y-18314 was effective in inhibiting *Pencillium italicum* decay on grapefruit, oranges and other citrus fruit cultivars. As in the case of *Pencillium digitatum*, NRRL Y-18314 more effectively controlled *Pencillin italicum* in grapefruits than in oranges. NRRL Y-18314 was also effective in inhibiting the development of *Geotrichum candidum* in citrus fruits. However, as shown in Table III, *Geotrichum candidum* was controlled to a lesser extent than the Penicillia decays, particularly in lemons.

EXAMPLE II

The ability of *Pichia guilliermondii* NRRL Y-18314 to inhibit Rhizopus rot development in grapes was demonstrated.

A biologically pure culture of NRRL Y-18314 was isolated and purified as described in Example I.

NRRL Y-18314 was incubated in 100 ml of NYDB in 250 ml Erlenmeyer flasks on a rotary shaker (100 rpm) at 28° C. for 48 hours. Freshly harvested grapes of the Perlette and Thompson Seedless cultivars were dipped momentarily in a suspension of the organism in NYDB. The berries were treated as whole clusters with non-injured berries, as injured berries which had been removed from the stems by pulling and thereby causing a wound, or as injured single berries wounded by piercing non-injured berries with a needle. Control berries were dipped in sterile NYDB only.

One to two hours after the berries had been dipped in the suspension, the berries were dried and thereafter inoculated by dipping in an aqueous suspension containing spores of the targeted pathogen at a concentration of $1 \times 10^4$ spores/ml. Alternatively, the berries were inoculated by placing a single decayed berry in the center of a group of non-injured berries; i.e. "nesting". The treated berries were placed in polyethylene-covered cartons and held at room temperature for 5 days. Whole treated clusters were placed directly in commercial shipping cartons.

Decay incidence was determined by counting the number of infected berries. Each treatment in each experiment consisted of at least three replicates of 20 berries or four replicates of five intact clusters placed in half of a shipping carton.

The results are shown in FIG. 1. As shown in FIG. 1, *Pichia guilliermondii* was effective in reducing Rhizopus rot in both injured and non-injured grape berries. Reduction of decay was most pronounced in berries that were not injured prior to inoculation and inoculated by nesting.

EXAMPLE III

The effectiveness of isolate of *Pichia guilliermondii* NRRL Y-18314 to inhibit *Botrytis cinerea* and *Pencillium expansum* rot was tested on apples.

Golden Delicious apples were washed with 2% sodium hypochlorite to surface sterilize the fruit. After air drying, the apples were placed on styrofoam trays in plastic trays with lids. Water (100 ml) was added to each tray for humidity. The apples were wounded using a needle. Wound size was 4mm wide by 5mm deep. Three-day old shake cultures of NRRL Y-18314 growing on NYDB at a $1 \times 10^9$ CFU/ml concentration were added to the wounds, 50 microliters/wound. Apples were allowed to air dry. Thereafter, an aqueous suspension of *Botrtyis cinerea* or *Penicillium expansum* spores, $1 \times 10^4$ spores/ml, were added to the wounds, 20 microliters/wound. Controls were inoculated with water only.

Figure 2:
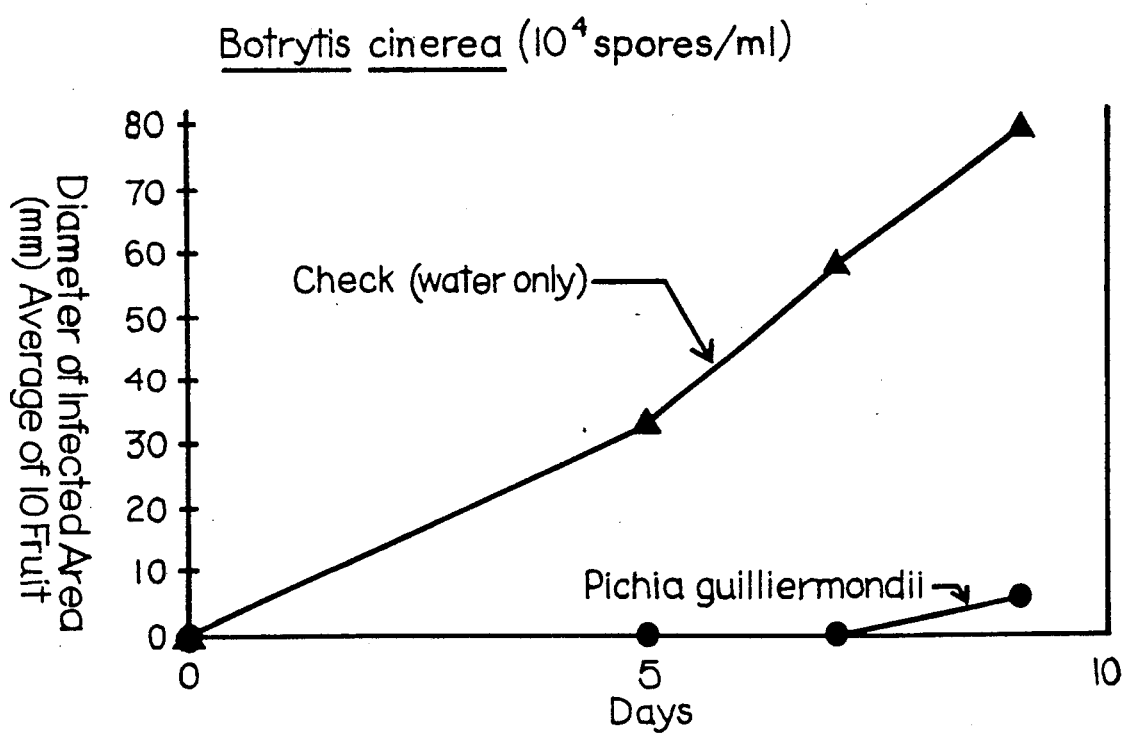
FIG. 2 is a line graph of the rot diameter area (mm) on apples infected with *Botrytis cinerea* vs. time (days), for: (1) control samples treated with water only, and; (2) samples treated with NRRL Y-18314.
Figure 3:
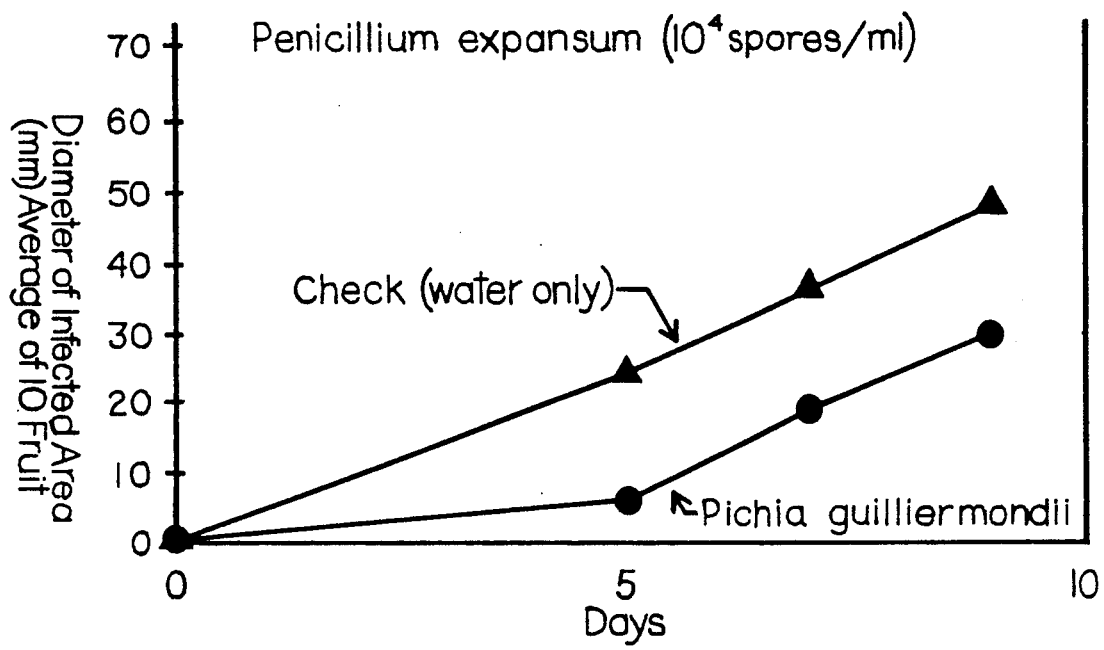
FIG. 3 is a line graph of rot diameter area (mm) on apples infected with *Penicillium expansum* vs. time (days) for: (1) control samples treated with water only, and; (2) samples treated with NRRL Y-18314.

Measurements of infected areas were taken 5, 7, 9 days after inoculation. Results are shown in FIGS. 2 and 3.

NRRL Y-18314 effectively controlled both *Botrytis cinerea* and *Penicillium expansum* rots in apples. As shown in FIG. 2, total protection against *Botrytis cinerea* occurred in treated apples up to about 7 days after inoculation, with only small lesion development after nine days. Protection against *Pencillium expansum* was to a lesser extent than against *Botrytis cinerea*. Nevertheless, FIG. 3 clearly shows that apples treated with NRRL Y-18314 had a significant decrease in the development of *Pencillium expansum* when compared to the untreated controls.

EXAMPLE IV

The effectiveness of *Pichia guilliermondii* NRRL Y-18314, to inhibit *Penicillium digitatum* on grapefruit was compared to the effectiveness of eight previously identified isolates of *D. hansenii*.

The eight isolates were obtained from the American Type Culture Collection, hereinafter referred to as "ATCC," located at 12301 Parklawn Drive, Rockville, Md., 20252, USA. Identification of the isolates tested were as follows: ATCC 18538, ATCC 20220, ATCC 36239, ATCC 34022, ATCC 36239, ATCC 9367, ATCC 36767, and ATCC 18107.

Each isolate tested was incubated in NYDB liquid medium at 28° C. for 48 hours. Following centrifugation, the resulting pellets were washed twice with water and thereafter suspended in water. Concentrations of the aqueous suspensions ranged from $1.3 \times 10^7$ to $1.3 \times 10^9$ CFU/ml.

The surface of the grapefruit was sterilized with 95% ethanol and placed on moist paper in $50 \times 100 \times 15$ cm plastic trays, 24 fruits per tray. Thereafter, the surface of the fruit was wounded using a needle. Two to four conical wounds, 3 mm deep, were cut in the fruit peel. An aqueous suspension of an isolate was brushed onto the surface of the wound. Each isolate was tested on 48 sites of inoculations. One to two hours later, an aqueous suspension of *Penicillium digitatum*, $1 \times 10^5$ spores/ml, was added to the wounds, 20 microliters/wound. Controls were inoculated with water only.

Figure 4:
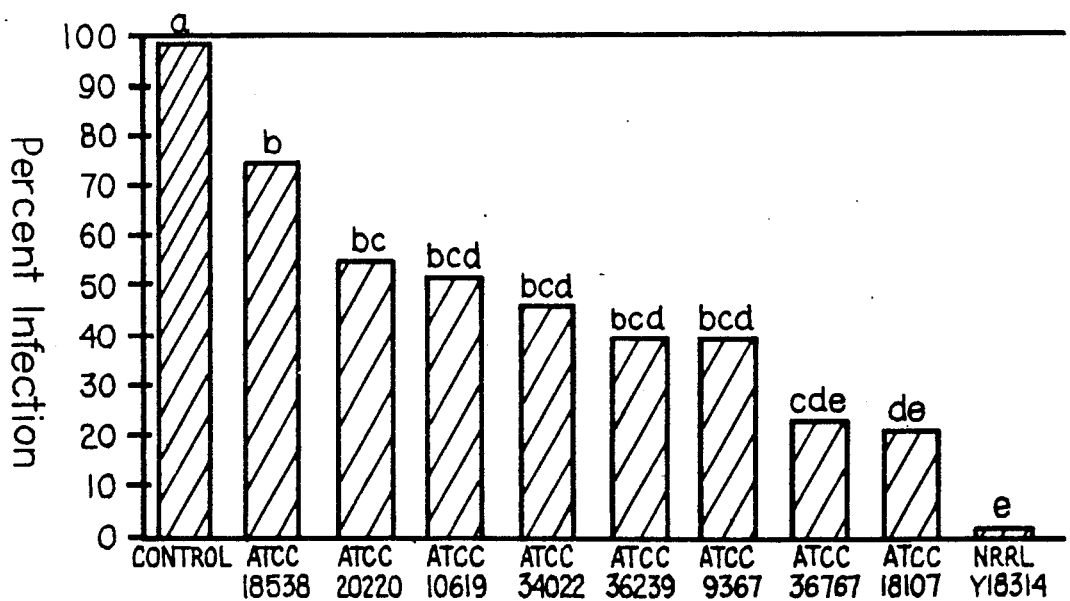
FIG. 4 is a bar graph of percent infection showing relative effectiveness of yeast isolates in inhibiting *Penicillium digitatum* decay on grapefruit.

The percent of fruit infection was recorded 7 days after inoculation. The data was analyzed by analysis of variance and means were separated by Duncan's Multiple Range Test. Values followed by different letters are significantly different at a 1% level. The results are shown in FIG. 4.

NRRL Y-18314 clearly exhibited superior control of *Penicillium digitatum* when compared to prior identified isolates of *D. hansenii*. After seven days of inoculation, total protection occurred in grapefruits inoculated with NRRL Y-1831 while as much as 25 to 65% infection occurred in fruits inoculated with isolates obtained from the ATCC.

The foregoing detailed descriptions and examples are given merely for purposes of illustration. Modifications and variations may be made therein without departing from the spirit and scope of the invention.

We claim:

1. A biologically pure culture of at least one isolate of *Pichia guilliermondii* having the identifying characteristics of an isolate selected from the group consisting of NRRL Y-18313, NRRL Y-18314, and NRRL Y-18654.

2. The biologically pure culture of claim 1 having the identifying characteristics of NRRL Y-18313.

3. The biologically pure culture of claim 1 having the identifying characteristics of NRRL Y-18314.

4. The biologically pure culture of claim 1 having the identifying characteristics of NRRL Y-18654.

* * * * *